US009332945B2

(12) United States Patent  
Kodaira

(10) Patent No.: US 9,332,945 B2  
(45) Date of Patent: May 10, 2016

(54) X-RAY CT SYSTEM

(71) Applicants: Kabushiki Kaisha Toshiba, Minato-ku (JP); Toshiba Medical Systems Corporation, Otawara-shi (JP)

(72) Inventor: Yasuo Kodaira, Utsunomiya (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 93 days.

(21) Appl. No.: 14/344,197

(22) PCT Filed: Feb. 20, 2013

(86) PCT No.: PCT/JP2013/054148  
§ 371 (c)(1),  
(2) Date: Mar. 11, 2014

(87) PCT Pub. No.: WO2013/125569  
PCT Pub. Date: Aug. 29, 2013

(65) Prior Publication Data  
US 2014/0254746 A1      Sep. 11, 2014

(30) Foreign Application Priority Data

Feb. 22, 2012    (JP) ................................. 2012-036195

(51) Int. Cl.  
*A61B 6/03*      (2006.01)  
*F16J 15/32*     (2006.01)  
(Continued)

(52) U.S. Cl.  
CPC ... *A61B 6/03* (2013.01); *A61B 6/44* (2013.01); *F16J 15/3204* (2013.01); *A61B 6/035* (2013.01);  
(Continued)

(58) Field of Classification Search  
CPC ... A61N 5/00; A61N 5/10; A61N 2005/0632; A61N 2005/0664; A61N 2005/0667; A61N 2005/1092; A61B 6/00; A61B 6/02; A61B 6/03; A61B 6/032; A61B 6/035; A61B 6/44; A61B 6/4429; A61B 6/4435; A61B 6/4447; B32B 2581/00; F16J 15/00; F16J 15/02; F16J 15/04; F16J 15/32; F16J 15/3204; F16J 15/3216; B01D 29/00; B01D 29/0002; B01D 29/0004; B01D 29/0007; B01D 29/0027; B01D 29/0043; B01D 29/0045; B01D 29/0093; B01D 29/0097; B01D 29/01; B01D 29/014; B01D 29/114; B01D 29/13; B01D 29/15; B01D 29/44; B01D 39/00; B01D 39/10; B01D 39/12; B01D 39/14; B01D 39/16; B01D 39/1692; B01D 39/20; B01D 39/2027; B01D 39/2041; B01D 46/4236; B01D 46/4263  
USPC .............. 378/4, 189, 197, 204, 210; 277/312, 277/315, 590, 628, 634, 637, 644, 647, 650, 277/916, 918, 920  
See application file for complete search history.

(56) References Cited

U.S. PATENT DOCUMENTS 5,761,269 A      6/1998  Sugihara et al.  
2004/0228450 A1*  11/2004 Mueller ........................ 378/199  
(Continued)

FOREIGN PATENT DOCUMENTS

JP          3-18346 U      2/1991  
JP          4-17840        1/1992  
(Continued)

OTHER PUBLICATIONS

International Search Report issued May 14, 2013, in PCT/JP13/054148 filed Feb. 20, 2013.

*Primary Examiner* — Anastasia Midkiff  
(74) *Attorney, Agent, or Firm* — Oblon, McClelland, Maier & Neustadt, L.L.P.

(57) ABSTRACT

An X-ray CT system including: a rotator including an X-ray tube installed therein; a gantry, arranged on a floor part, and configured to rotatably support the rotator; a cover configured to cover the rotator and the gantry from the outside; and an elastic member, and mounted along the lower edge of the cover, having restoring force, and configured to elastically be in contact with the floor part against the restoring force. The X-ray CT system can reduce noise from inside of the cover.

9 Claims, 8 Drawing Sheets

(51) Int. Cl.
  *A61B 6/00*   (2006.01)
  *A61N 5/06*   (2006.01)
  *A61N 5/10*   (2006.01)
  *F16J 15/02*  (2006.01)
  *B01D 29/00*  (2006.01)
  *B01D 46/42*  (2006.01)

(52) U.S. Cl.
  CPC ............. *A61B 6/4429* (2013.01); *A61B 6/4488* (2013.01); *A61N 2005/0664* (2013.01); *A61N 2005/0667* (2013.01); *A61N 2005/1092* (2013.01); *B01D 29/0045* (2013.01); *B01D 46/4236* (2013.01); *B01D 46/4263* (2013.01); *B32B 2581/00* (2013.01); *F16J 15/02* (2013.01); *F16J 15/32* (2013.01)

(56) References Cited

U.S. PATENT DOCUMENTS

2006/0215808 A1*  9/2006  Lacey .............................. 378/19
2013/0167310 A1*  7/2013  Eungard ........................ 14/71.1

FOREIGN PATENT DOCUMENTS

| JP | 5-288453    | 11/1993 |
| JP | 8-257008    | 10/1996 |
| JP | 9-276262    | 10/1997 |
| JP | 10-234721   | 9/1998  |
| JP | 11-337131   | 12/1999 |
| JP | 2003-190136 | 7/2003  |
| JP | 2009-28259  | 2/2009  |
| JP | 2011-24866  | 2/2011  |
| JP | 5159965     | 3/2013  |

* cited by examiner

X-RAY CT SYSTEM

TECHNICAL FIELD

The embodiments of the present invention relate to an X-ray CT system.

BACKGROUND ART

Conventionally, X-ray CT systems detect X-rays, which are irradiated from an X-ray tube and transmitted a subject, and reconstruct an image based on a result of the detection to obtain an X-ray tomographic image.

The X-ray tube is provided inside an annular rotator. The annular rotator is supported rotatably by a gantry. The gantry is mounted on a floor part. Around the annular rotator and the gantry is covered with a cover.

There are systems, as medical diagnosis systems, which arrange sound absorbing members on an inner surface of a cover of an MRI system, in order to increase a silencing effect and decrease noise from the inside of the system (Patent Document 1).

There is a space between the floor part and the lower edge of the cover. The space has a variation. Since the variation is due to product precision and assembling precision of the cover, as well as surface precision of the X-ray CT system setting place (floor part), it is difficult to completely eliminate the space.

PRIOR ART DOCUMENT

Patent Document

[Patent Document 1] Japanese Unexamined Patent Application Publication No. 8-257008

SUMMARY OF THE INVENTION

Problems to be Solved by the Invention

Noise passing through the space between the floor part and the lower edge of the cover is leaked from the inside of the cover to the outside. Meanwhile, if the lower edge of the cover is contacted to the floor part, abnormal sounds are generated because of the vibration during the operation. The noise generated from the inside of the cover includes wind noise while the annular rotator is rotating, noise of a motor driving the rotator, and the like.

In addition, it is considered that the space between the floor part and the lower edge of the cover can be closed by utilizing silencing members according to Patent Document 1. However, it is difficult to close the space, which varies in size, by utilizing the silencing members, so that there was a problem such that the noise from the inside of the cover could not be sufficiently reduced.

The embodiments of the present invention are intended to solve the above-described problem, to provide an X-ray CT system being able to reduce the noise from the inside of the cover sufficiently.

Means for Solving the Problems

In order to solve the above-described problem, the X-ray CT system of the embodiments comprises a rotator, a gantry, a cover, and an elastic member. An X-ray tube is arranged inside of the rotator. The gantry is placed on a floor part, and rotatably supports the rotator. The cover covers the rotator and the gantry from outside. The elastic member is mounted along the lower edge of the cover, has restoring force, and is elastically in contact with the floor part against the restoring force.

MODES FOR CARRYING OUT THE INVENTION

Figure 1:
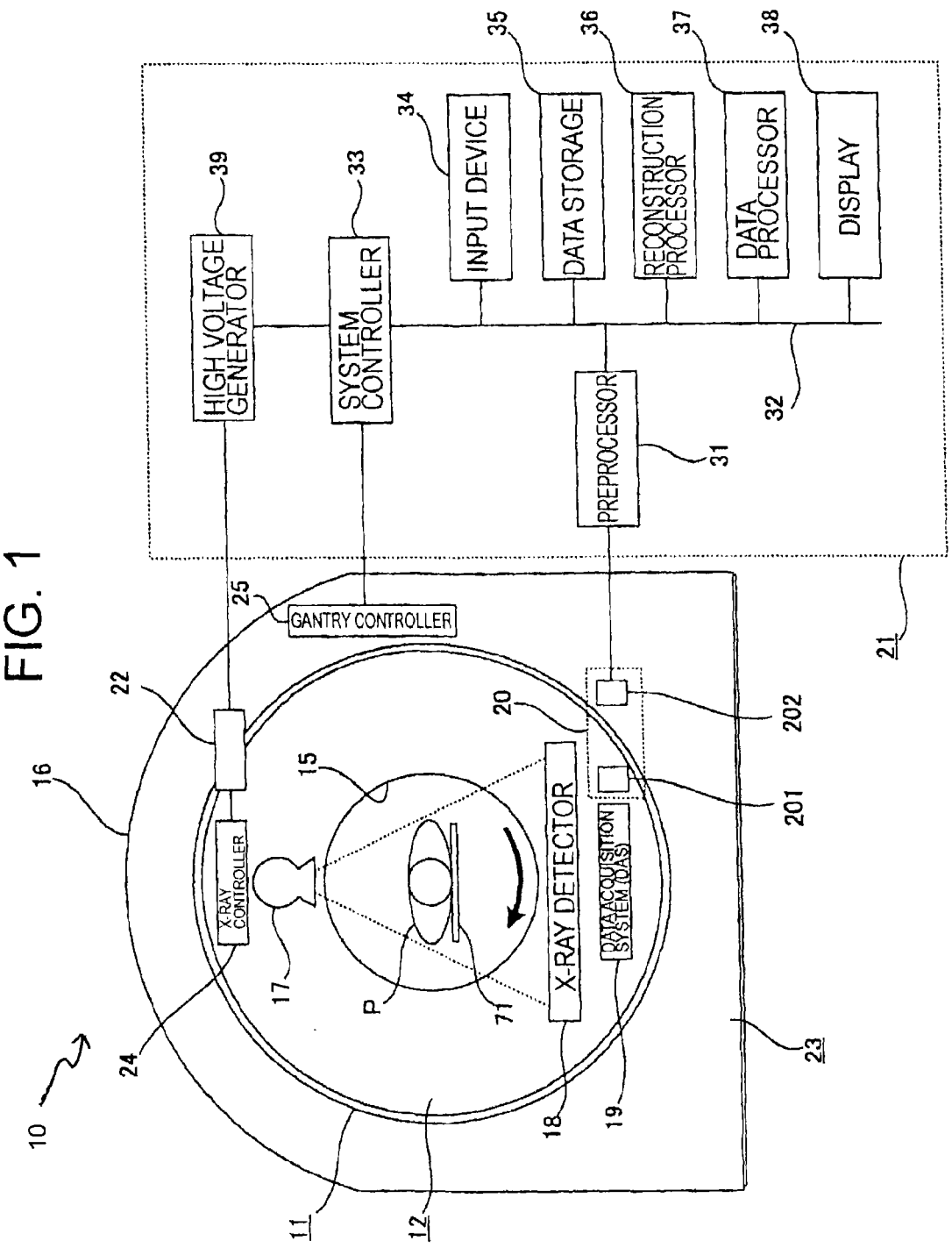
FIG. 1 is a block diagram of an X-ray CT system according to an embodiment.

An embodiment of the X-ray CT system is described with reference to FIG. 1. FIG. 1 is a block diagram of the X-ray CT system.

In FIG. 1, as the X-ray CT system, an example of an X-ray CT system for medical diagnosis is displayed. An X-ray CT system 10 comprises a gantry 11, an annular rotator 12, rotating mechanisms 14, a cover 16, coolers 40, and a duct 50.

Inside of the gantry 11, the annular rotator 12 and the rotating mechanisms 14 are provided. The annular rotator 12 is rotated by the rotating mechanisms 14.

Inside of the annular rotator 12, an X-ray tube 17 and ax X-ray detector 18 are provided. At the center of the gantry 11 and the annular rotator 12, an aperture 15 is provided in order to insert a subject P placed on a top 71 of a couch 70 from front of the gantry and rotator.

The cover 16 is formed to cover the gantry 11 and the annular rotator 12. The detail description of the cover 16 will be described later.

The X-ray tube 17 and the X-ray detector 18 are arranged facing each other around the aperture 15. X-rays are irradiated from the X-ray tube 17 to the subject P. The X-rays transmitted the subject P are detected and then converted into an electric signal by the X-ray detector 18. The electric signal is amplified and converted into digital data by a data acquisition system (DAS) 19. The detail description of a mechanism to cool the X-ray tube 17 (cooling mechanism) will be described later.

The X-ray detector 18 includes multiple detection element arrays configuring with, for example, scintillator arrays, and photodiode arrays, and is arrayed along an arc around a focus point of the X-ray tube 17. Further, the digital data (projection data) from the DAS 19 is transmitted to a console 21 via a data transmitter 20.

The data transmitter 20 transmits the projection data from the annular rotator 12 to the console 21 in a non-contact manner, comprises a sender 201 provided on the annular rotator 12 side and a receiver 202 provided on a fixed part of the gantry 11, and supplies the data received by the receiver 202 to the console 21. Further, the sender 201 is installed to an annular rotator, and the receiver 202 is installed to an annular fixed part.

Furthermore, a slip ring 22 and an X-ray controller 24 are provided to the annular rotator 12, and a gantry controller 25 is provided to a fixed part 23.

The console 21 constitutes a computer system, and the projection data from the data transmitter 20 is supplied to a preprocessor 31. The preprocessor 31 performs preprocessing, such as data correction, on the projection data, and outputs the processed data to a bus line 32.

The bus line 32 is connected to a system controller 33, an input device 34, a data storage 35, a reconstruction processor 36, a data processor 37, a display 38, and the like, and the system controller 33 is connected to a high voltage generator 39.

The system controller 33 functions as a host controller, and controls operations of each unit of the console 21, as well as controlling the gantry controller 25 and the high voltage generator 39. The data storage 35 stores data, such as tomographic images, and the reconstruction processor 36 reconstructs three-dimensional image data from projection data. The data processor 37 processes the stored image data in the data storage 35 and the reconstructed image data. The display 38 displays the data obtained by image data processing, and the like.

The input device 34 includes a keyboard, a mouse, and the like, is operated by a user (doctor, operator, and the like), and performs various settings for data processing. The input device 34 is also input various information such as states of the subject and examination methods.

The high voltage generator 39 controls the X-ray controller 24 via the slip ring 22, and supplies electricity to the X-ray tube 17 to provide required power (tube voltage, tube current) for X-ray irradiation. The X-ray tube 17 generates beam X-rays spreading toward two directions including a slice direction parallel to the axial direction of the subject P and a channel direction orthogonal thereto. The spreading angle of the beam X-rays in the slice direction may be referred to as a cone angle, and the spreading angle thereof in the channel direction may be referred to as a fan angle.

<Cover>

The primary structure of the X-ray CT system has been described above.

Figure 2:
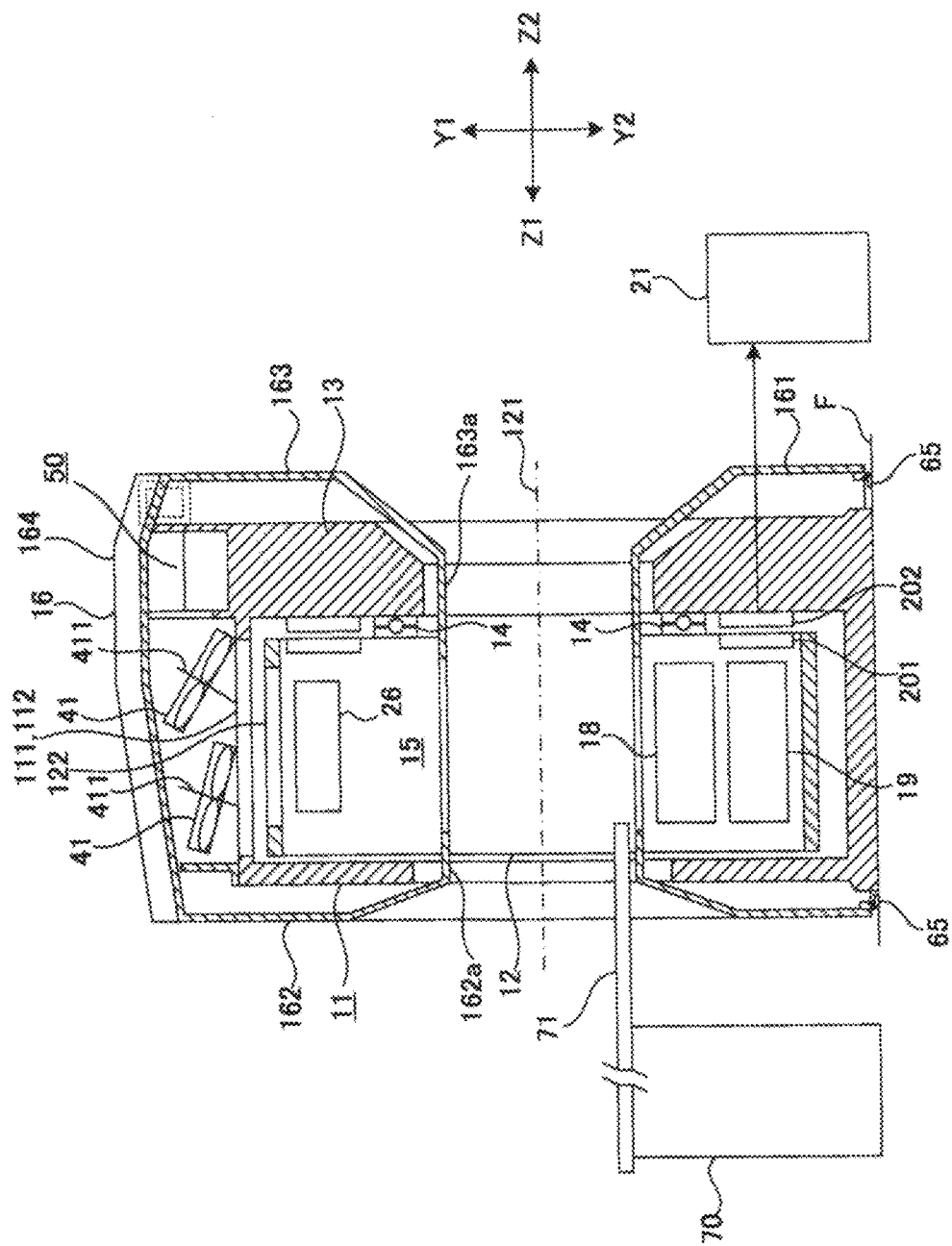
FIG. 2 is a cross-sectional view of the X-ray CT system when the system is cut in the radiation direction around a body axis.

Next, the detail description of the cover 16 is described with reference to FIGS. 2 to 4. FIG. 2 is a cross-sectional view of the X-ray CT system when the system is cut in the radiation direction centering the body axis, FIG. 3 is an elevation view of the X-ray CT system, and FIG. 4 is a perspective view of the X-ray CT system as seen from a diagonally backward thereof.

Here, parts of the gantry 11 arranged in the front part, rear part, both sides, upper part, and lower part of the annular rotator 12 may be referred to as a front surface part, a rear surface part, side surface parts, a ceiling part, and a bottom part, respectively. Further, a longitudinal direction (both sides direction), a vertical direction (height direction), and a axial direction (front-rear direction) may be referred to as an X-axis direction, Y-axis direction, and Z-axis direction, respectively. Furthermore, the rear surface of the gantry 11 may be referred to as a frame 13.

Figure 3:
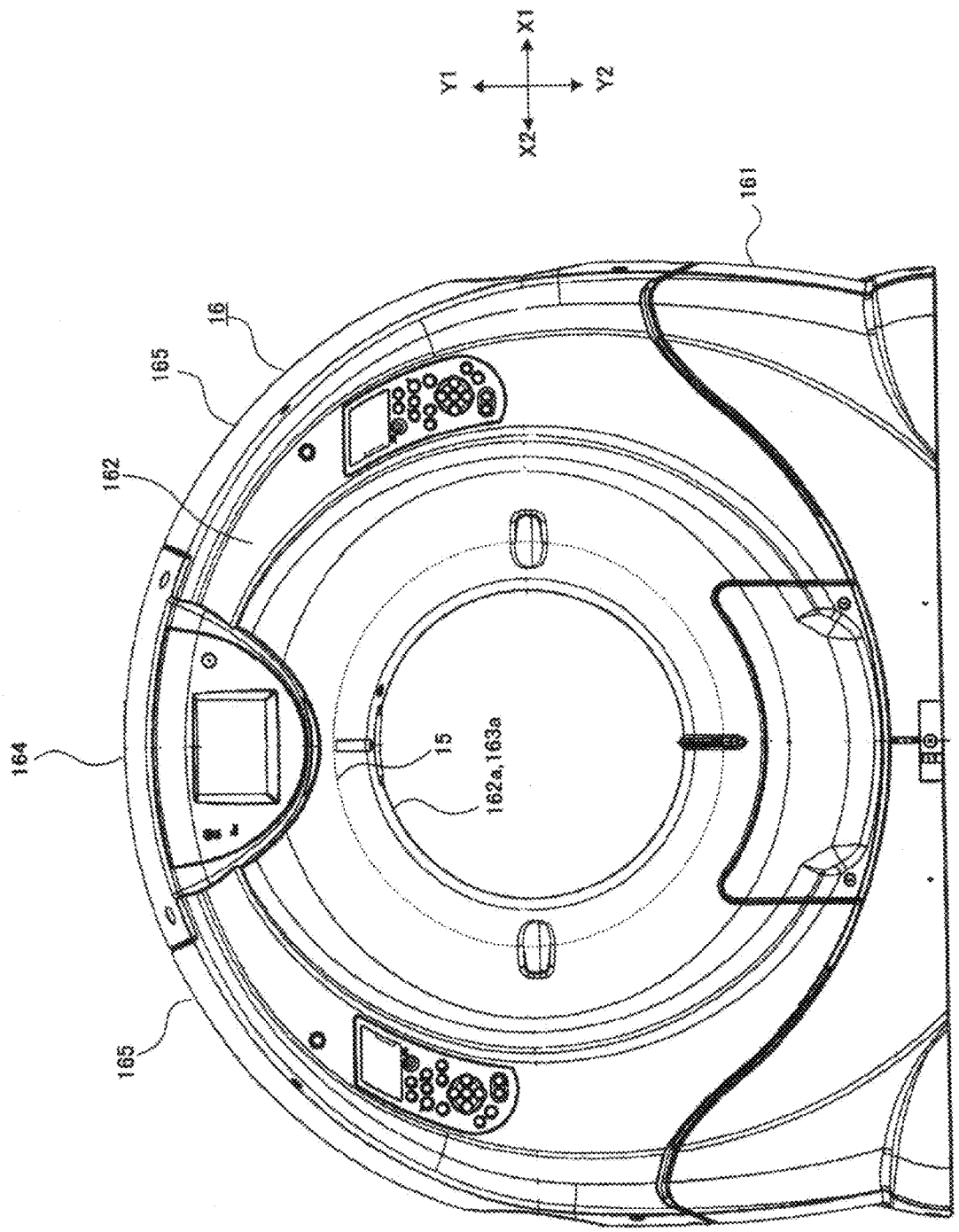
FIG. 3 is an elevation view of the X-ray CT system.
Figure 4:
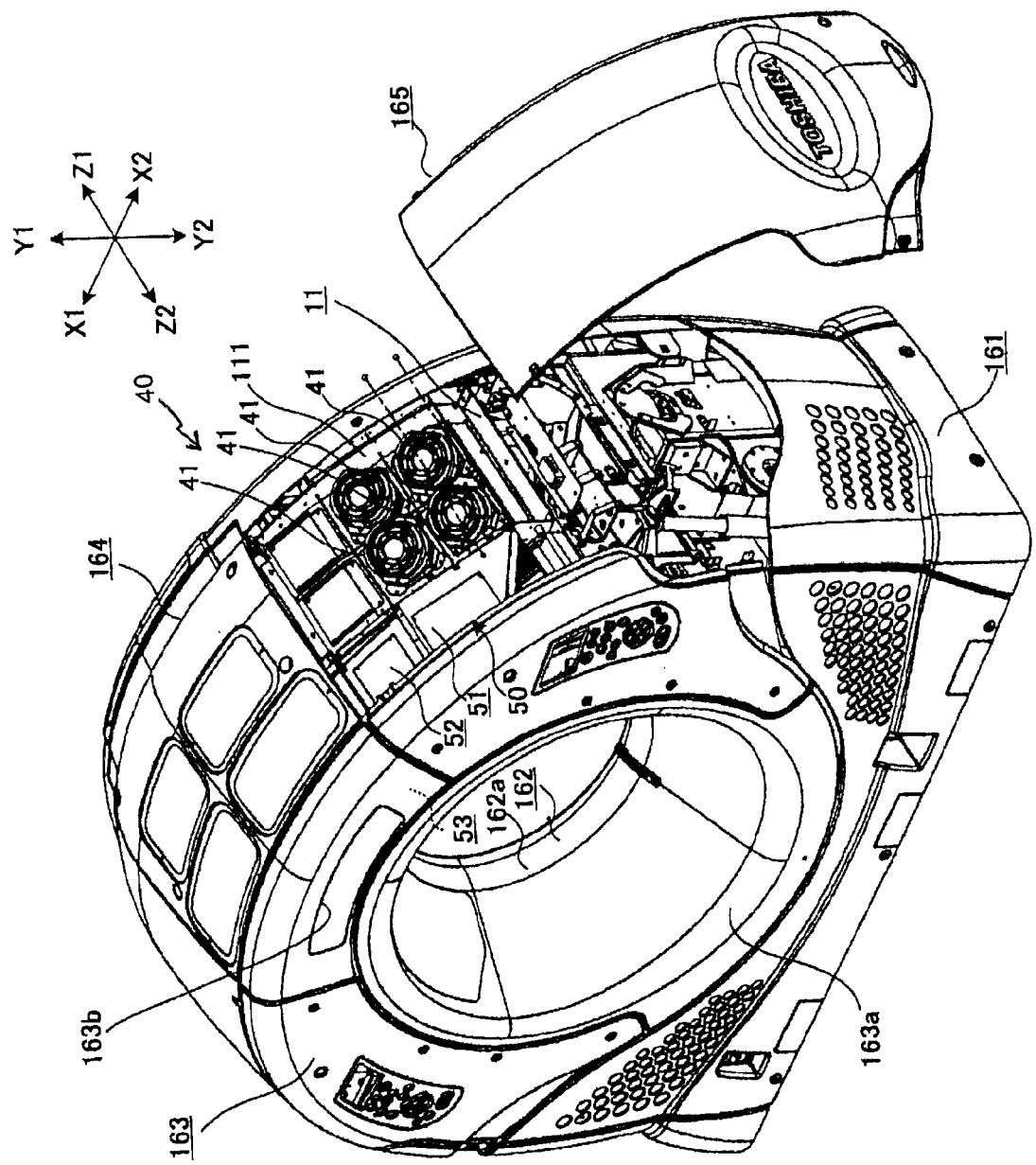
FIG. 4 is a perspective view of the X-ray CT system as seen from a diagonally backward thereof.

In addition, in FIGS. 2 to 4, the front side and rear side of the annular rotator 12 are denoted as Z1 and Z2, respectively, the right side and left side thereof are denoted as X1 and X2, respectively, and the upper side and lower side thereof are denoted as Y1 and Y2, respectively.

As shown in FIGS. 2 to 4, the cover 16 comprise a bottom cover 161 covering the bottom part of the gantry 11, a front cover 162 covering the front surface part thereof, a rear cover 163 covering the rear surface part thereof, a ceiling cover 164 covering the ceiling part thereof, and side covers 165 covering the side surfaces thereof.

The front cover 162 has a cylinder-opening front part 162a. The cylinder-opening front part 162a is formed in a cylindrical shape, and fitted from front to the aperture 15 to cover an approximately front half of the aperture 15 from the Z-axis direction (axial direction).

The rear cover 163 has a cylinder-opening rear part 163a. The cylinder-opening rear part 163a is formed in a cylindrical shape, and fitted from rear to the aperture 15 to cover an approximately rear half of the aperture 15 from the Z-axis direction. The cylinder-opening front part 162a and the cylinder-opening rear part 163a configure a cylindrical side part.

On the upper part of the rear cover 163, an exhaust port 163b is arranged in order to exhaust heat from a radiator 26 which will be described later, to the outside of the cover 16. The exhaust port 163b is arranged at a position of 12 o'clock shown in FIG. 4. Since the heat from the radiator 26 is risen inside the cover 16, it makes it possible to exhaust the heat effectively from the exhaust port 163b arranged on the upper part of the rear cover 163. The noise from the inside of the cover 16, which is transmitted to the front side of the X-ray CT system via the exhaust port 163b, is reduced comparing to the case when the exhaust port 163b is arranged at the front surface part of either the front cover 162 or the bottom cover 161.

In order to exhaust the heat effectively from the radiator 26, the exhaust port 163b may be arranged on the upper part of the cover 16. For example, the exhaust port 163b may be arranged on the ceiling cover 164.

Some parts of the duct 50, which will be described later, are covered with the rear cover 163. Further, fan 41, which will be described later, and other parts of the duct 50, are covered with the side covers 165. The fan 41 and the other parts of the duct 50 may be covered with other cover 16, for example, the ceiling cover 164.

<Cooler and Duct>

The cooler 40 has the fans 41. The fans 41 are arranged in the vicinity of the radiator 26, and send the heat from the radiator 26 to the duct 50. The duct 50 is arranged between the gantry 11 and the cover 16, and sends exhaust air received from the fans 41 to the exhaust port 163b. The noise generated from the inside of the cover includes wind noise while the fans 41 are rotating, and noise of a motor driving the fans 41.

<Soundproof Structure>

Figure 5:
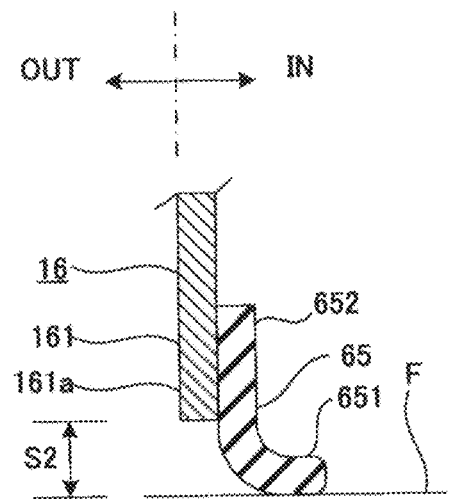
FIG. 5 is a cross-sectional view of a soundproof structure.

Next, a soundproof structure to reduce the noise from inside of the cover 16 is described with reference to FIG. 2 and FIG. 5. FIG. 5 is a cross-sectional view of the soundproof structure.

As shown in FIG. 2 and FIG. 5, there is a space S2 between the X-ray CT system setting place (floor part F) and a lower edge 161a of the bottom cover 161.

The floor part F in the present embodiment is a floor of a building if the X-ray CT system is arranged directly on the floor of the building. The floor part F is the table if a strong table is placed on the floor of the building and the X-ray CT system is arranged thereon.

An elastic member 65 is arranged to close the space between the lower edge 161a of the bottom cover 161 and the floor part F. FIG. 5 shows a cross-sectional form of the elastic member 65 when the member is cut from the direction orthogonal to the direction along the lower edge 161a of the bottom cover 161.

The elastic member 65 is formed in a belt-like shape by materials having elasticity. An example of a material used for the elastic member includes natural rubber, synthetic rubber, silicone rubber, polyurethane rubber, and sponge rubber. The elastic member 65 is formed from one or in combination of two or more of the above materials.

Examples of the synthetic rubber include chloroprene rubber, nitrile rubber, ethylene propylene rubber, fluoro rubber, and styrene-butadiene rubber.

Examples of sponge rubber include natural sponge rubber, chloroprene sponge rubber, nitrile sponge rubber, fluoro sponge rubber, silicone sponge rubber, polyurethane sponge rubber, expanded polyethylene rubber, and poron rubber.

The elastic member 65 is mounted along the entire periphery of the lower edge 161a of the bottom cover 161. When the X-ray CT system is arranged on the floor part F, a tip-end part 651 of the elastic member 65 is in contact with the floor part F and bent inward from the bottom cover 161 to be elastically in contact with the floor part F against a restoring force of the elastic member 65.

Even there is a variation in the space between the lower edge 161a of the bottom cover 161 and the floor part F, it is possible to close the space with the elastic member 65. By closing the space S2 with the elastic member 65, it is possible to reduce the noise from the inside of the cover 16.

In addition, whereas the tip-end part 651 of the elastic member 65 is in contact with the floor part F, the lower edge 161a of the bottom cover 161 is not contacted thereto. Therefore, it is possible to reduce vibration noise generated while the system is in operation by the elastic member 65 absorbing the vibration of the cover 16 during the system operation.

The tip-end part 651 of the elastic member 65 is formed to bend inward of the bottom cover 161 (IN direction shown in FIG. 5). Since the tip-end part 651 of the elastic member 65 is hidden inside of the bottom cover 161, it is possible to improve appearance quality of the system.

(Modified Example)

Figure 6:
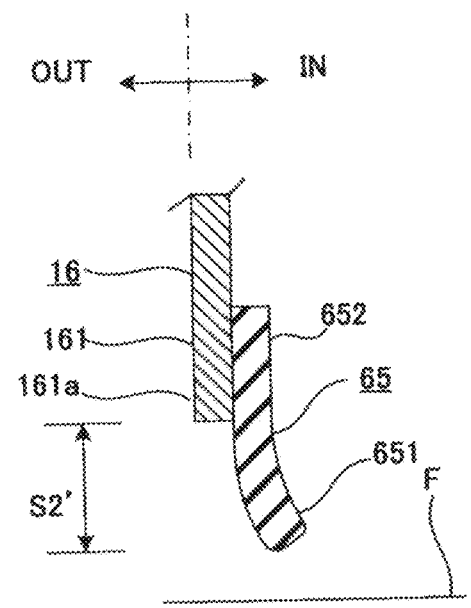
FIG. 6 is a cross-sectional view of an elastic member before being in contact with a floor part, in a modified example.

Next, it is described a modified example of the elastic member 65 with reference to FIG. 6. FIG. 6 is a cross-sectional view of the elastic member 65 before being in contact with the floor part F. FIG. 6 shows a cross-sectional form of the elastic member 65 when the member is cut from the direction orthogonal to the direction along the lower edge 161a of the bottom cover 161 (same in FIG. 7). FIG. 6 also shows a distance S2', which is the distance from the lower edge 161a of the bottom cover 161 to the tip-end part 651 of the elastic member 65. The distance S2' is longer than the space S2 (see FIG. 5) (S2'>S2).

As shown in FIG. 6, the tip-end part 651 of the elastic member 65 is curved inward from the bottom cover 161 (IN direction shown in FIG. 6) in advance so as to bend thereto. Thereby, when the tip-end part 651 is in contact with the floor part F, the tip-end part 651 receives force directed toward the bending direction (inward direction) of the bottom cover 161 from the floor part F and it makes easier for the tip-end part 651 to bend thereto.

(Other Modified Example)

Figure 7:
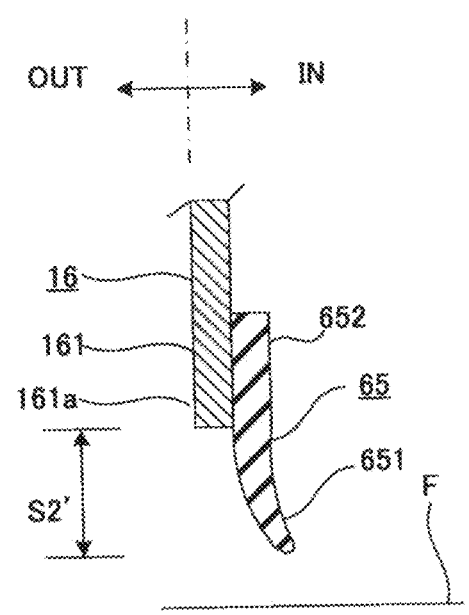
FIG. 7 is a cross-sectional view of an elastic member before being in contact with a floor part, in another modified example.

Next, other modified example of the elastic member 65 is described with reference to FIG. 7. FIG. 7 is a cross-sectional view of the elastic member 65 before being in contact with the floor part F.

As shown in FIG. 7, the tip-end part 651 of the elastic member 65 is formed with a tapered tip. The plate thickness of the elastic member 65 is thinner than that of the other parts including a base-end part 652. Thereby, the tip-end part 651 is easier to bend when the tip-end part 652 is in contact with the floor F.

(Other Soundproof Structure)

Figure 8:
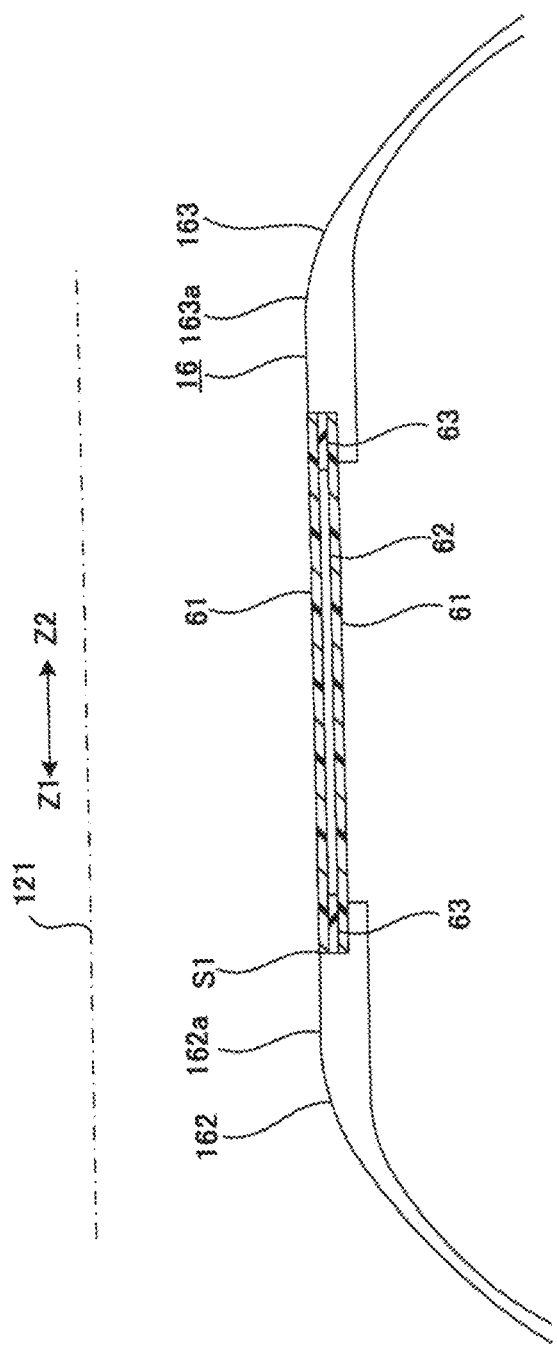
FIG. 8 is a cross-sectional view of an aperture when the aperture is cut along the axial direction (Z-axis direction).

Next, other soundproof structure is described with reference to FIG. 2 and FIG. 8. FIG. 8 is a cross-sectional view of the aperture 15 when the aperture is cut along the axial direction (Z-axis direction).

As shown in FIG. 8, the other soundproof structure comprises two soundproof members 61 and a soundproof layer 62. Thereby it makes possible to improve sound insulation performance. The soundproof layer 62 is configured by an air layer.

As shown in FIG. 8, the two soundproof members 61 are arranged in such a way that the air layer as the soundproof layer 62 is sandwiched therebetween. The two soundproof members 61 are arranged to bridge over X-ray transmitting ports S1.

(Soundproof Member)

The soundproof member 61 is a material having a large sound transmission loss, and is configured from a thin film-like material, having a good laser transmittance with respect to a laser for X-rays and marking. Thereby, deterioration in quality of images obtained by radiography can be suppressed.

As kinds of the soundproof member 61, it is included a sound absorbing member in which a part of the acoustic energy is converted to heat energy to deaden a reflected sound, and a sound reflecting member having properties of reflecting and refracting an incident sound.

As examples of the sound absorbing member, a fiber-like member and a sponge-like member having many small holes therein are used, and as a representative example of the material used for the sound absorbing member, it is preferable to use a porous material, such as glass wool and urethane.

The sound reflecting member, for example, may be configured by encapsulating gas, such as helium, having acoustic velocity greater than that of air, into between the two soundproof members.

In the present embodiment, for example, polyethylene terephthalate (PET) is used as the soundproof members 61. As PET, it is preferable to use Mylar®.

(Air Layer)

As described above, the air layer as the soundproof layer 62 is sandwiched between the two soundproof members 61. By providing the air layer, it is possible to improve a sound insulating property. In addition, by thickening of the air layer, a frequency at which a coincidence effect occurs is decreased. Here, the coincidence effect is a phenomenon such that a sound transmission loss value is decreased at a specific frequency.

It is possible to increase the sound transmission loss value and improve the sound insulting property by thickening the soundproof members 61. Here, the sound transmission loss value is an amount ten times the logarithm of the reciprocal of sound transmittance, and represented by decibels [dB]. In addition, the sound transmittance is a ratio of transmitted sound intensity to incident sound intensity.

It is possible to improve the sound insulation effect by stacking the two soundproof members 61. It is also possible to improve the sound insulting property from the low-pitched tone to the intermediate-pitched tone due to the effectiveness of the air layer thickness.

By utilizing a double-sided tape 63, air tightness of the air layer is improved, therefore, the improvement of the sound insulting property can be realized.

The thickness of the air layer can be changed by changing the plate thickness of the double-sided tape 63. Thereby, the frequency is set to be less than or equal to the specified frequency at which the coincidence effect occurs. In addition, the two soundproof members 61 may be arranged to form a specific angle therebetween. In this case, the plate thickness of the double-sided tape 63 may be different between at a rear-end part 162d side of the cylinder-opening front part 162a and at a front-end part 163d side of the cylinder-opening rear part 163a.

In the present embodiment, the sound absorbing member may be installed to the inner surface of the cover 16. As an example of the sound absorbing member, a porous material formed in a high-density plate shape, such as rock wool and glass wool, is used. As representative examples of the porous materials, it is preferable to use thin films, such as polyethylene and vinyl film.

Further, in the present embodiment, a sound reflecting member having properties of reflecting and refracting an incident sound may be installed to the inner surface of the cover 16.

(Other Embodiment)

In the embodiment described above, it has been described about the soundproof members 61 for improving the sound insulation effect by closing the space S2 between the lower edge 161a of the bottom cover 161 and the floor part F. The space S2 is for taking outside air into the inside of the cover 16. When the space S2 is closed completely by the soundproof members 61, the sound insulating property is improved, however, taking outside air into the inside of the cover 16 via the space S2 becomes difficult (air permeability is degraded) and releasing the heat therefrom to the outside becomes also difficult, thereby deteriorating a heat radiation property. On the other hand, if outside air is easily taken into the inside via the space S2, even dust included in the outside air is also taken inside of the cover 16. Therefore, it is easy for the dust to be pooled inside of the cover, and dust resistance becomes poor.

In this embodiment, it is preferable for the soundproof members 61 to be members, which do not deteriorate the heat radiation property as well as not degrading dust resistance, and more preferably to be members having an X-ray-resistance property.

Figure 9:
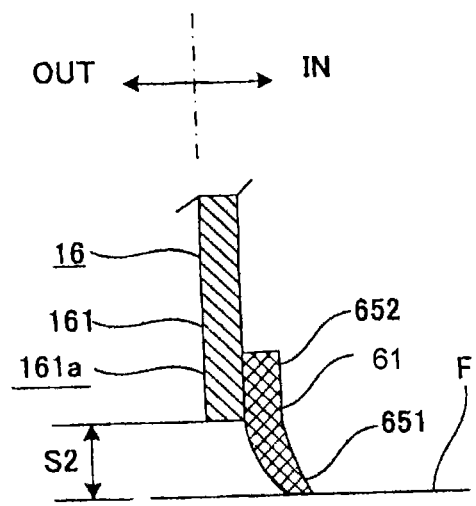
FIG. 9 is a partial cross-sectional view of an X-ray CT system according to other embodiment.

FIG. 9 is a partial cross-sectional view of an X-ray CT system according to the other embodiment. As shown in FIG. 9, in this embodiment, an air filter as the soundproof member 61 is arranged to close the space S2.

For example, the air filter has a mesh shape formed by a resin fiber having the X-ray-resistance property or a metal wire. Further, a wire material in which metal coating is performed on to a resin fiber may be used.

As a resin fiber having the X-ray-resistance property, for example, at least one among silicone rubber, polychloroprene, chlorosulfonated polyethylene, chlorinated polyethylene, nitrile rubber, ethylene propylene rubber, and the like is used.

The shape of the mesh formed by those resin fiber or metal wire is represented by a number of the meshes, which is the number of fibers or wires with regard to 2.54 cm in length, and an aperture ratio, which is a percentage of a space in a unit area.

In one example, the number of the meshes is 10 to 150 and the aperture ratio thereof is 40% to 60%.

When the number of meshes is less than 10, an obstacle occurs in the performance of the heat radiation property (air permeability), and when the number of meshes is over 150, an obstacle occurs in the performance of the dust resistance. When the aperture ratio is less than 40%, an obstacle occurs in the performance of the heat radiation property (air permeability), and when the aperture ratio is over 60%, an obstacle occurs in the performance of the dust resistance.

EXPLANATION OF SYMBOLS

P Subject
S1 X-ray transmitting port
S2 Space
10 X-ray CT system
11 Gantry
111 Fan setting part
112 Communication port
12 Annular rotator
121 Body axis
122 Vent hole
13 Frame
14 Rotating mechanism
15 Aperture
16 Cover
161 Bottom cover
161a Lower edge
162 Front cover
162a Cylinder-opening front part
163 Rear cover
163a Cylinder-opening rear part
163b Exhaust port
164 Ceiling cover
165 Side cover
17 X-ray tube
18 X-ray detector
19 Data acquisition system (DAS)
20 Data transmitter
21 Console
22 Slip ring
23 Fixed part
24 X-ray controller
25 Gantry controller
26 Radiator
31 Preprocessor
32 Bus line
33 System controller
34 Input device
35 Data storage
36 Reconstruction processor
37 Data processor
38 Display
39 High voltage generator
40 Cooler
41 Fan
50 Duct
61 Soundproof member
62 Soundproof layer
63 Double-sided tape
65 Elastic member
651 Tip-end part
652 Base-end part
70 Couch
71 Top

The invention claimed is:

1. An X-ray CT system comprising:
   a rotator having an X-ray tube installed therein;
   a gantry, arranged on a floor part, and configured to rotatably support the rotator;
   a cover configured to cover the rotator and the gantry from the outside; and
   an elastic member, mounted along a lower edge of the cover, and configured to elastically be in contact with the floor part against a restoring force of the elastic member.

2. The X-ray CT system according to claim 1, wherein the elastic member is arranged to close a space between the lower edge of the cover and the floor part.

3. The X-ray CT system according to claim 1, wherein the elastic member comprises a tip-end part being in contact with the floor part and bending inwardly from the lower edge of the cover.

4. The X-ray CT system according to claim 3, wherein the tip-end part of the elastic member is bent inwardly from the cover before being brought into contact with the floor part.

5. The X-ray CT system according to claim 3, wherein the tip-end part of the elastic member is formed to be a tapered tip.

6. The X-ray CT system according to claim 1, wherein the elastic member is formed by one or more of a natural rubber, synthetic rubber, silicone rubber, polyurethane rubber, and sponge rubber.

7. An X-ray CT system comprising:
- a rotator having an X-ray tube installed therein;
- a gantry, arranged on a floor part, and configured to rotatably support the rotator;
- a cover configured to cover the rotator and the gantry from outside; and
- an air filter, mounted along a lower edge of the cover, and arranged to close a space between the lower edge and the floor part.

8. The X-ray CT system according to claim 7, wherein the air filter is formed by a resin material having an X-ray-resistance property.

9. The X-ray CT system according to claim 7, wherein the air filter is formed by metal meshes.

\* \* \* \* \*